United States Patent [19]

Ho

[11] 4,425,280
[45] Jan. 10, 1984

[54] METAL AMINO ACIDS

[75] Inventor: Benedict Y. K. Ho, Sagamore Hills, Ohio

[73] Assignee: Ferro Corporation, Cleveland, Ohio

[21] Appl. No.: 249,161

[22] Filed: Mar. 30, 1981

[51] Int. Cl.$^3$ ............................................. C07F 3/06
[52] U.S. Cl. ........................... 260/429.9; 260/429 R; 260/429.7; 260/438.1; 260/414; 260/435 R; 562/553; 548/104; 524/238
[58] Field of Search ............. 260/429.9, 429.7, 435, 260/429 R, 414, 326.14 T; 562/553; 524/238; 548/104

[56] References Cited

U.S. PATENT DOCUMENTS

| | | | |
|---|---|---|---|
| 2,781,372 | 2/1957 | Mannheimer | 562/553 |
| 2,840,603 | 6/1958 | Mock et al. | 260/429 R X |
| 2,883,406 | 4/1959 | Jezl | 260/429.9 |
| 3,008,814 | 11/1961 | Robbins | 44/63 |
| 3,037,997 | 6/1962 | Hewitt | 260/435 R |
| 3,102,107 | 8/1963 | Solder | 524/238 |
| 3,662,026 | 5/1972 | Rushton | 524/238 |
| 3,780,095 | 12/1973 | Klemm et al. | 260/448 R |
| 4,093,639 | 6/1978 | Habermeier et al. | 260/429.9 |
| 4,254,016 | 3/1981 | Onizawa | 524/238 |
| 4,312,815 | 1/1982 | Wilson et al. | 260/429.9 |

*Primary Examiner*—Helen M. S. Sneed
*Attorney, Agent, or Firm*—Baldwin, Egan, Walling & Fetzer

[57] ABSTRACT

A composition of matter comprising metal complexes of aminocarboxylic-carboxylic acids. The composition may be used as polyvinal halide stabilizers.

13 Claims, No Drawings

METAL AMINO ACIDS

BACKGROUND OF THE INVENTION

Vinyl halide polymers, in particular polyvinyl chloride, are commonly used in both plasticized and unplasticized forms. Making these forms often subjects the polymer to high temperatures during processing. The processing of vinyl halide polymers requires the addition of one or more stabilizers to prevent degradation of polyvinyl halide, as evidenced by gross color change or "burning". Burning is the term used to describe the darkening of the vinyl material from a light or clear to black color. This color change is the product of thermal decomposition through dehydrohalogenation. In addition, the polymer exhibits an inferior mechanical quality after dedydrohalogenation as evidenced by an increase in brittleness.

In addition to the degradative effects of heat, vinyl halide polymers are discolored on extended exposure to light as often occurs in outdoor applications.

In commercial practice, several types of stabilizers have been employed to avoid this degradation. Organo-tin stabilizers have been employed with satisfactory results. However, organotin stabilizers are costly, and the supply of tin assures that the price will continue to increase. Some toxicity problems are also present in the use of certain organotin stabilizers. A combination of barium and cadmium carboxylate and phenate stabilizers have been used, exhibiting good stabilization properties, but not without some problems. There are toxicity problems associated with cadmium stabilizers in both the production of the stabilizers and in the end use. In fact, recent government actions, both in the United States and abroad, indicate a movement toward decreasing the allowable workplace exposure level to cadmium. Antimony stabilizers such as antimony mercaptides have also been used to prevent degradation. Lead carboxylates have effected excellent results as stabilizers for vinyl halide resins. However, the end use toxicity and production level toxicity associated with lead compounds is well known.

Zinc and calcium carboxylate combinations have been employed as stabilizing agents. However, such combinations have not been free of difficulties. Most zinc compounds used either alone or in combination as stabilizers lead to rapid degradation or "burning" of polyvinyl halides after a very short period of good color. In order to achieve acceptable stabilizing performance from zinc-calcium combinations, many co-additives or co-stabilizers must be employed, thereby increasing the cost of the stabilizer systems.

Therefore, while the use of zinc compounds as stabilizing agents for vinyl halide polymers is desirable in order to avoid the toxicity problems inherent in barium-cadmium and lead stabilizers and the expense problems associated with organotin stabilizers, there has been no fully acceptable way to achieve long term stabilization with zinc compound stabilizers.

However, the use of zinc compounds as stabilizers for vinyl halide resins has many advantages. First, zinc is basically non-toxic, and therefore avoids the inherent toxicity problems associated with cadmium and lead stabilizers. There appear to be no toxicity problems associated with zinc compounds at either the production level or in the end use level.

Second, zinc compounds exhibit excellent stability against photodegradation. While tin mercaptides produce acceptable results as stabilizers, zinc compounds are far superior in their ability to stabilize polyvinyl halides against the degradative effects of light.

Third, zinc produces no staining problems that often occur with cadmium, lead, antimony, and tin stabilizers. Airborne sulfur compounds react with cadmium stabilizers to produce undesirable color.

Fourth, zinc metal is much less expensive than tin metal, and zinc is more available than either cadmium or tin. The future availability of zinc appears promising.

Accordingly, it is an objective of this invention to provide novel zinc compounds with activity as light and heat stabilizers for vinyl halide polymers.

It is a further objective of this invention to provide novel zinc compounds which avoid the rapid degradation of polyvinyl chloride after short periods of exposure to heat or extended exposure to light.

Yet, another objective of this invention is to provide novel metallic amino acid complexes which have stabilizing capabilities for vinyl halide polymers.

The method of accomplishing these and other objectives will become apparent in the following description of the invention.

SUMMARY OF THE INVENTION

This invention relates to metal amino acid complexes and their use as polyvinyl halide stabilizers with the general formula:

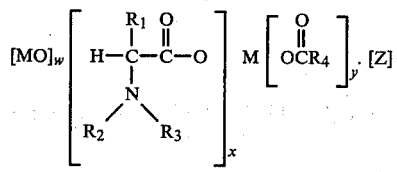

wherein
w has a value of 0 to 2;
x has a value of 1 or 2;
y has a value of 0 or 1; and $(x+y=2)$
M is a member selected from the group consisting of zinc, magnesium, calcium, barium, strontium, manganese, cadmium, lead, tin II, tin IV $(R_5)_2$ where $R_5$ is a lower alkyl of $C_1-C_8$;
$R_1$ is a member selected from the group consisting of H—, $C_1-C_{12}$ alkyl,

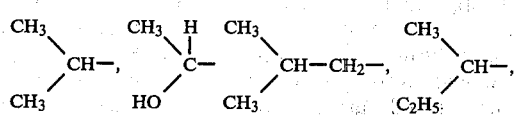

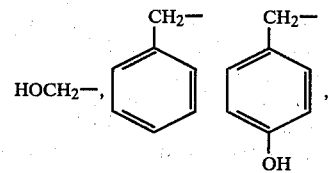

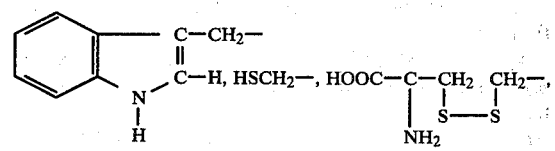

-continued

HOOC—CH$_2$—, HOOCCH$_2$CH$_2$—, CH$_3$OOCCH$_2$CH$_2$—,

H$_2$NOC—CH$_2$—, H$_2$NOC—CH$_2$—CH$_2$—,

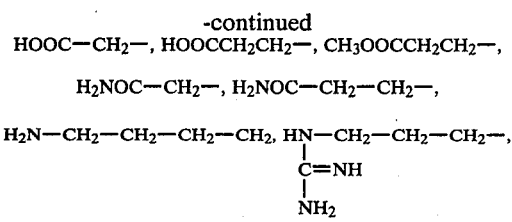

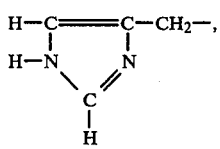

and CH$_3$SCH$_2$CH$_2$— with the proviso that R$_1$ can not be CH$_3$SCH$_2$CH$_2$— when M is zinc, and x=1 and y=1;

R$_2$ is a member selected from the group consisting of H, CH$_2$CH$_2$OH, C(CH$_2$OH)$_3$, an alkyl of C$_1$–C$_{15}$, an aryl, and substituted aryl ring;

R$_3$ is a member selected from the group consisting of H and CH$_2$CH$_2$OH;

R$_4$ is a member selected from the group consisting of an alkyl of C$_1$–C$_{20}$, straight chain or branched, an aryl and substituted aryl ring, and Z is 0-1 molecules or partial molecules of a carboxylic acid corresponding to

DETAILED DESCRIPTION OF THE INVENTION

It is important to note that the compounds of this invention are described as mixed ligands or metal chelates of amino acids containing one or two molecules of amino acid. The stabilizers can be carefully distinguished from known stabilizers in that the chelation is done internally before use or on the same molecule. This is in contrast to the known use of external chelation of zinc molecules by the addition of chelating agents to known zinc stabilizers in the polymer as in Japanese Publication Patent Bulletin 1977: 19,744. This present invention results in the intentional chelating of zinc through amino acids.

It is important to realize that the chelator or ligand must control the production or activity of zinc chloride generated during heating of polyvinyl chloride. Hydrochloric acid, produced by dehydrohalogenation, interacts with metal stabilizers to produce metal halides which accelerate the degradation of polyvinyl chloride. If the control of the metal activity is achieved through an external chelator, the chelation is the result of a more or less random process whereby the chelator finds a metal molecule. However, with internal chelation, the production and activity of metal halide in the polymer can be more closely controlled. Therefore, internal chelation results in better stabilizers for polyvinyl halides, in particular, polyvinyl chloride and copolymers thereof.

U.S. Pat. No. 3,983,085 to Yoshida et al., discloses both internal and external chelating agents. Due to the fact that external chelation is involved, sufficient control of the activity of the metal halide is not achieved. Also, the acylation of the basic amino acid is remote from the chelation site. The added presence of an amide linkage may produce over-chelation in that the metal amino acid salt is not active enough to produce acceptable stabilization. The acylation of the basic amino acid also introduces an additional step in the preparation of the materials, thereby increasing costs.

Japanese Public Patent Bulletin 1979: 55,047 discloses mixed ligand compounds of amino acid metal salts with alkyl, alkoxy and hydroxy groups. This patent bulletin does not disclose or suggest the use of carboxylates as an additional active ligand on the metal atom, or an activator. Carboxylates perform better as activators than alkyl, alkoxy or hydroxyl groups. In addition, carboxylates should confer greater stability to the stabilizing compound.

The metal amino acids useful as polyvinyl halide stabilizer complexes have the general formula I:

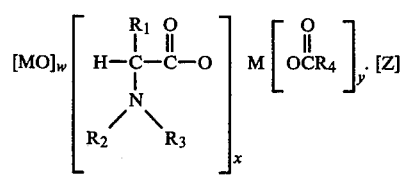

wherein w has a value of 0 to 2;

x has a value of 1 or 2;

y has a value of 0 or 1; and x+y=2;

M is a member selected from the group consisting of zinc, magnesium, calcium, barium, strontium, manganese, cadmium, lead, tin II and tin IV (R$_5$)$_2$, where R$_5$ is lower alkyl of C$_1$–C$_8$;

R$_1$ is a member selected from the group consisting of

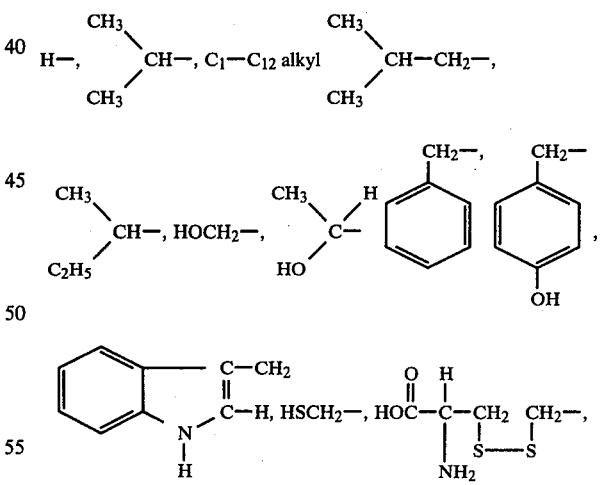

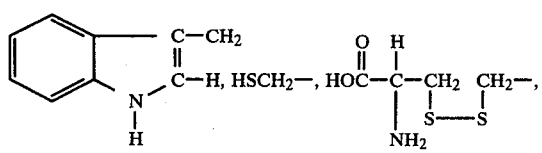

HOC—CH$_2$—, HOOCCH$_2$CH$_2$—, CH$_3$OOCCH$_2$CH$_2$—,

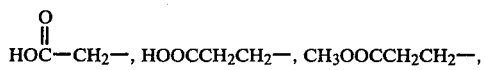

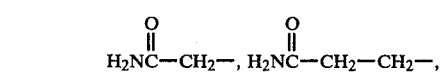

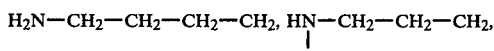

$$H-C=\!\!=\!\!=C-CH_2-,$$
with N-NH ring closed by CH below (imidazole-like), 5

$R_2$ is a member selected from the group consisting of H, $CH_2CH_2OH$, $C(CH_2OH)_3$, an alkyl of $C_1-C_{15}$, an aryl and a substituted aryl ring;

$R_3$ is a member selected from the group consisting of H and $CH_2CH_2OH$;

$R_4$ is a member selected from the group consisting of alkyls of $C_1-C_{20}$, straight chain or branched, an aryl ring and a substituted aryl ring;

Z is 0–1 molecules or partial molecules of a carboxylic acid corresponding to $$HO\overset{O}{\underset{\|}{C}}R_4.$$

Among the various amino acid metal compositions covered by the previous generic structure are included novel mixed ligand compositions having the following formula II:

$$[MO]_w \left[ H-\overset{R_1}{\underset{\underset{R_2\;R_3}{N}}{C}}-\overset{O}{\underset{\|}{C}}-O \right] M \left[ \overset{O}{\underset{\|}{OCR_4}} \right] \quad (Z)$$

wherein w has a value of 0 to 2;

M is a member selected from the group of divalent metals consisting of zinc, magnesium, calcium, barium, strontium, manganese, cadmium, lead tin II, tin IV $(R_5)_2$ where $R_5$ is a lower alkyl of $C_1-C_8$;

$R_1$ is a member selected from the group consisting of H—, $C_1-C_{12}$ alkyl—, $$\begin{array}{c}CH_3\\ \diagdown\\ CH_3\end{array}\!\!CH-,\quad \begin{array}{c}CH_3\\ \diagdown\\ CH_3\end{array}\!\!CH-CH_2-,\quad \begin{array}{c}CH_3\\ \diagdown\\ C_2H_5\end{array}\!\!CH-,$$

$HOCH_2-$, $\underset{HO}{\overset{CH_3}{\underset{}{C}}}\!\!\!\overset{H}{\underset{}{-}}\!\!-CH_2-\!\!\bigcirc$, $-CH_2-\!\!\bigcirc\!\!-OH$, indole-CH$_2$- (3-indolylmethyl), $HSCH_2-$, $HOOC-\underset{\underset{S-\!\!-\!\!S}{NH_2}}{\overset{H}{\underset{|}{C}}}-CH_2\;\;CH_2-$, $HOOC-CH_2-$, $HOOC-CHCH_2-$, $CH_3OOCCH_2CH_2-$,
$H_2NOC-CH_2-$, $H_2NOC-CH_2-CH_2-$,
$H_2N-CH_2-CH_2-CH_2-CH_2-$, $$HN-CH_2-CH_2-CH_2-$$
$$\underset{NH_2}{\overset{|}{C}=NH}$$

$$H-C=\!\!=\!\!=C-CH_2-,\text{ and } CH_3SCH_2CH_2-;$$
(with H—N, N ring, CH closing)

and $CH_3SCH_2CH_2-$ with the proviso that $R_1$ cannot be $CH_3SCH_2CH_2-$ when M is zinc;

$R_2$ is a member selected from the group consisting of H, $CH_2CH_2OH$, $C(CH_2OH)_3$, an alkyl of $C_1-C_{15}$, an aryl and a substituted aryl ring.

$R_3$ is a member selected from the group consisting of H and $CH_2CH_2OH$;

$R_4$ is a member selected from the group consisting of alkyls of $C_1-C_{20}$, straight chain or branched, an aryl ring and a substituted aryl ring;

Z is 0–1 molecule or partial molecules of carboxylic acid corresponding to $$HO\overset{O}{\underset{\|}{C}}R_4.$$

Also included are bis amino acid metal complexes of the following formula III.

$$\left[ HC\!\!\underset{\underset{R_2\;\;R_3}{N}}{\overset{R_1}{-}}\!\!\overset{O}{\underset{\|}{C}}-O \right]_2 M$$

wherein:

M is a member selected from the group of divalent metals consisting of zinc, magnesium, calcium, barium, strontium, manganese, cadmium, lead, tin II, tin IV $(R_4)_2$ where $R_4$ is a lower alkyl of $C_1-C_8$;

$R_1$ is a member selected from the group consisting of H—, $C_1-C_{12}$ alkyl, $$\begin{array}{c}CH_3\\ \diagdown\\ CH_3\end{array}\!\!CH-,\; HOCH_2-,\; \underset{HO}{\overset{CH_3\;H}{\underset{}{C}}}\!\!-,\; \begin{array}{c}CH_3\\ \diagdown\\ CH_3\end{array}\!\!CH-CH_2-,$$

$$\begin{array}{c}CH_3\\ \diagdown\\ C_2H_5\end{array}\!\!CH-,\quad -CH_2-\!\!\bigcirc,\quad -CH_2-\!\!\bigcirc\!\!-OH,$$

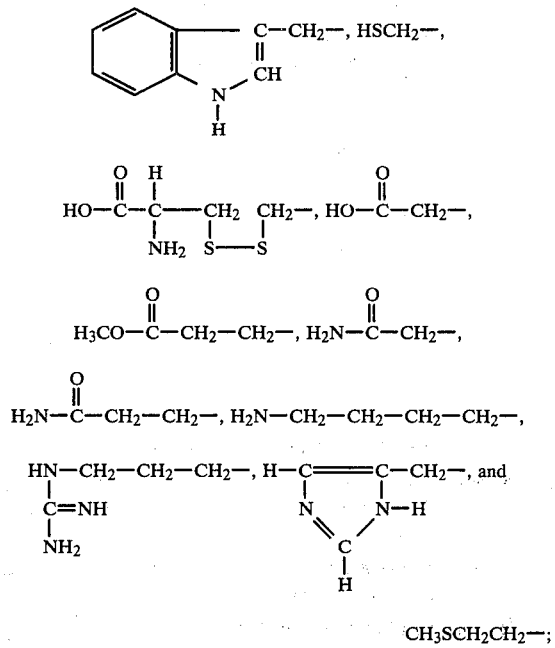

R₂ is a member selected from the group consisting of H, CH₂CH₂OH, C(CH₂OH)₃, an alkyl of $C_1$–$C_{15}$, an aryl and a substituted aryl; and R₃ is a member selected from the group consisting of H, and CH₂—CH₂OH with the proviso that if R₂ is hydrogen, then R₃ cannot be hydrogen.

Zinc monoglutamate has been disclosed as a stabilizer for polyvinyl chloride in Jones, U.S. Pat. No. 3,652,619. However, zinc monoglutamate does not display sufficient activity when used alone as a stabilizer.

Zinc bis (glutamate) displays the same structural features as a mixed ligand compound as in general formula I where Y=0 and X=2.

Zinc bis (glutamate) is disclosed in "The Preparation and Isolation of Metallo Glutamic Acid Complexes" by David Sabine and Sr. Helen Therese Nyberg and Michael Cefola published in *Archives of Biochemistry and Biophysics* pg. 166–168 (1974 Ed.). We have found, surprisingly, that this compound stabilizes polyvinyl halides.

Vinyl halide polymers may be used in various forms such as profile, siding, pipe, bottles, and flexible films or sheets. As can be appreciated, various end uses determine the level of acceptability for the performance of a polyvinyl halide stabilizer. For instance, the performance level of a stabilizer in a flexible film formulation may not need to be as high as that required for a siding formulation because of higher heat or more strenuous processing conditions in the latter case and because of various end use conditions such as exposure to light.

Various tests have been devised to compare performance levels of polyvinyl halide stabilizers. The most useful parameters derived from the various testing methods are the time to the first color appearance and time to blackness. The time to first color appearance is the amount of time required to produce a noticeable color change in the polymer. The time to blackness is the time required to totally burn or darken or blacken the polymer.

The static oven test is merely the subjecting of the polymer to a certain temperature inside an oven. Periodic checks of the polymer, approximately every 15 minutes, are taken, and the results are recorded.

A particularly helpful test in determining the efficacy of a stabilizer is the Metrastat test, a variation of the static oven test. In the Metrastat test, a strip of the polymer formulation is subjected to a certain temperature in an oven and is removed from the oven on a conveyor at a predetermined rate. Therefore, it is possible to determine more closely both the time to first color appearance and to total darkness or total blackness of the stabilized formulation by relating the position of the color change on the strip to the time that part of the strip remained in the oven.

The dynamic two-roll mill test is particularly helpful in determining whether or not a stabilizer will be effective in a formulation which will be subjected to calendering. A sample is milled on a two-roll mill, and samples are removed and recorded at periodic intervals, such as five minutes.

The Torque Rheometer test is utilized to determine the effectiveness of the stabilizer in formulations that will be subjected to an extrusion process. In fact, the Torque Rheometer test is, in effect, an imitation of an extrusion process wherein a sample is fused, and samples are removed for observation of color periodically, for example every two minutes after fusion.

Typically, conventional stabilizers for vinyl halides are used in conjunction with co-stabilizers. The novel metal amino acid complexes described herein may also be used with co-stabilizers. Beta-diketones have heretofore been used as co-stabilizers in conventional zinc-calcium stabilizer formulations. Dehydroacetic acid has been used as a co-stabilizer previously. Use of dehydroacetic acid in conjunction with carboxylates is disclosed in U.S. Pat. No. 3,346,536 to Argus Chemical Corporation. Interestingly enough, this reference specifically excludes use with nitrogen-containing carboxylic acid compounds. However, the use of dehydroacetic acid as a co-stabilizer in conjunction with the novel metal amino acid complexes disclosed herein is particularly desirable.

Various other co-stabilizers can be used in combination with the dehydroacetic acid or other Beta-diketones co-stabilizers and the novel metal amino acid complexes. Phosphites, epoxides, antioxidants, alkaline earth organic salts, and polyols, are all suited for use as additional co-stabilizers in accordance with this invention.

Among the phosphites that are particularly useful in this invention are included tris-nonylphenyl phosphite, diphenylisodecyl phosphite, THOP, triphenyl phosphite, tridecyl phosphite, diphenyl mono (2-ethyl hexyl) phosphite, monophenyldiisodecyl phosphite, tricresyl phosphite, stearyl neopentylene phosphite, dineopentylene triethylene glycol phosphite, diphenyl phosphite, and monophenyl phosphite.

Typical epoxides used as co-stabilizers include epoxidized soybean oil and epoxidized linseed oil as well as epoxidized tall oil, epoxidized cottonseed oil, epoxidized palm oil, glycidyl p-methoxy phenyl ether, and cyclohexane oxide.

Antioxidants commonly employed as co-stabilizers include 2,6-ditertiary-butyl-4-methyl phenol, isopropylidene bisphenol, 2,6-di-t-butyl phenol, 2,4-di-t-butyl phenol, catechol, resorcinol, 2,6-di-t-butyl-4-methoxy phenol, as well as phenyl amines and thiodipropionic acid esters.

Alkaline earth organic salts typically utilized as co-stabilizers in connection with vinyl halide polymers include calcium stearate, barium stearate, barium nonyl phenate, calcium octoate, calcium benzoate, magnesium stearate, calcium aceto acetate, and strontium laurate.

Polyols that are commonly employed as co-stabilizers for vinyl halide polymers include pentaerythritol, dipentaerythritol, sorbitol, mannitol, and trimethylol propane.

Lubricants permit polyvinyl chloride to be worked and fused, yet avoid sticking to the rolls. Common lubricants include metallic fatty acid soaps, and various waxes.

Fillers, such as calcium carbonate, and pigments, such as titanium dioxide, are often added in the stabilizing formulation of conventional polyvinyl chloride stabilizers. Such fillers and pigments are readily adaptable for use in connection with the stabilizing compounds disclosed herein.

The following is a table disclosing various formulations of stabilizing compounds in connection with polyvinyl chloride for plasticized applications in parts per weight.

|   | I | II | III | IV | V |
|---|---|---|---|---|---|
| PVC | 100 | 100 | 100 | 100 | 100 |
| Plasticizer | 40 | 40 | 40 | 40 | 40 |
| Phosphite |   | 1 | 1 | 1 | 1 |
| Epoxide |   | 5 | 5 | 5 | 5 |
| Stabilizer | x | x | x | x |   |
| Organic co-stabilizer |   |   | y | y |   |
| Filler |   |   |   | 10 | 10 |
| TiO2 |   |   |   | 5 | 5 |
| Control Stabilizer |   |   |   |   | 2 |

The following is a table showing a specific formulation and parts per weight of ingredients of a stabilizing package for a rigid formulation of polyvinyl chloride.

|   | I | II | III | IV | V |
|---|---|---|---|---|---|
| PVC | 100 | 100 | 100 | 100 | 100 |
| CaStr2 |   | 1 | 1 | 1 | 1 |
| TiO2 |   |   |   | 5 | 5 |
| CaCO3 |   |   |   | 10 | 10 |
| Stabilizer | x | x | x | x |   |
| Organic co-stabilizer |   |   | y | y |   |
| Control Stabilizer |   |   |   |   | 2 |

The following examples will more clearly define the invention. However, the Examples are not intended to limit the scope of the invention.

EXAMPLE I

Several different reaction types may be utilized in order to form the novel metal amino acid complexes. The first reaction type is:

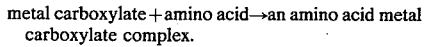

As an example of the above reaction type, zinc trimethylacetate (26.8 g) and glycine also known in the art as aminoacetic acid as named in Merck Index, 9th Ed., Merck & Company, 1976, #4325 (7.5 g) were placed in 600 ml of toluene in a one-liter, one-neck round-bottom flask equipped with a reflux condenser. The mixture was agitated by a magnetic stirrer and heated at refluxing temperature for twenty hours. The mixture was then filtered while still hot, and the filter cake was dried in a forced air oven. The reaction product was glycinatozinc trimethylacetate. Drying of the filtrate yielded a by-product identified by infrared spectroscopic method as trimethylacetic acid.

Similarly, glycinatozinc neodecanoate is prepared starting with zinc neodecanoate and glycine.

EXAMPLE II

The second reaction type is typified by the following equation:

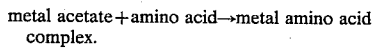

EXAMPLE II(a)

In a 500 ml one-neck round-bottom flask, 21.95 grams of zinc acetate and 14.62 grams of glutamine also known in the art as 2-amino glutaramic acid as named in Merck Index, 9th Ed., Merck & Company, 1976, #4304 were placed in 300 ml of toluene. The apparatus was equipped with a condenser and a Dean-Stark Trap. Following agitation by a magnetic stirrer, the solution was brought to reflux, and water was collected immediately in the Dean-Stark Trap. The solution was heated at the refluxing temperature for four hours, at which time the solid was filtered and dried, yielding a product of glutaminatozinc acetate.acetic acid.

EXAMPLE II(b)

37.5 grams of glycine and 109.75 grams of zinc acetate dihydrate were added to 120 ml of glacial acetic acid in a 500 ml, one-neck round-bottom flask. The apparatus was equipped with a reflux condenser and Dean-Stark Trap. Following agitation with a magnetic stirrer, the mixture was heated to dissolve all the solids. The volatiles were distilled off, and crystallization was induced upon cooling. The product, glycinatozinc acetate.acetic acid, was obtained upon filtration.

EXAMPLE II(c)

In a one liter, one-neck round-bottom flask equipped with a distillation head, reflux condenser and magnetic stirrer, 300 grams of glycine and 878 grams of zinc acetate dihydrate were added to 300 ml of water. A clear solution was obtained at 80° C. The solution was poured into a dish which was subsequently placed in a vacuum oven, thereby removing the volatiles. A friable white solid of glycinatozinc acetate.half-acetic acid was the product.

EXAMPLE II(d)

Glycinatozinc acetate.half-acetic-acid.10% calcium stearate was prepared by ball-milling the compound from Example II(c), together with 10% by weight calcium stearate overnight. Various quantities of metal stearates and various metal stearates may be substituted for the calcium stearate.

EXAMPLE II(e)

Tricinatozinc acetate was prepared by dissolving 17.9 grams of tricine also known in the art as N-[(trishydroxymethyl)methyl]glycine as named in Aldrich Catalog, Aldrich Chemical Company, P. O. Box 355, Milwaukee, Wis., P. 821, 1979-80 and 21.9 grams of zinc acetate dihydrate in 250 ml of water in a 500 ml, three-neck flask equipped with a magnetic stirrer and reflux condenser. The solution was refluxed for three hours at which time the solution appeared clear. The water was then evaporated to recover a solid product of tricinatozinc acetate with an NMR spectrum which indicated 1:1 mole ratio of tricinate to acetate.

EXAMPLE II(f)

Sarcosinatozinc acetate was prepared by reacting 8.9 grams of sarcosine also known in the art as N-methylaminoacetic acid as named in Merck Index, 9th Ed., Merck & Company, 1976, #8126 with 21.9 grams of zinc acetate dihydrate in 250 ml of water in a 500 ml, three-neck flask equipped with a magnetic stirrer and reflux condenser. The solution was refluxed for three hours at which time the solution appeared clear. Evaporation of the water yielded a solid product of sarcosinatozinc acetate with an NMR spectrum which indicated a 1:1 mole ratio of sarcosinate to acetate.

EXAMPLE II(g)

Methioninatozinc acetate was prepared by reacting 14.9 grams of methionine also known in the art as 2-amino-4-(methylthio)butyric acid as named in Merck Index, 9th Ed., Merck & Company, 1976, #5845 and 21.9 grams of zinc acetate dihydrate in 250 ml of water in a 500 ml three-neck flask equipped with a magnetic stirrer and reflux condenser. The solution was refluxed for three hours at which time the solution appeared clear. The water was evaporated and a solid product of methioninatozinc acetate was recovered.

EXAMPLE II(h)

Bicinatozinc acetate was prepared by reacting 16.3 grams of bicine also known in the art as N,N-bis(2-hydroxyethyl) glycine as named in Aldrich Catalog, Aldrich Chemical Company, P. O. Box 355, Milwaukee, Wis., P. 110, 1979-80 and 21.9 grams of zinc acetate dihydrate in 250 ml of water in a 500 ml three-neck flask equipped with a magnetic stirrer and reflux condenser. The solution was refluxed for three hours at which time the solution appeared clear. The water was then evaporated and a solid product of bicinatozinc acetate was recovered. An NMR spectrum indicated a 1:1 mole ratio of bicinate to acetate.

EXAMPLE II(i)

Tricinatocalcium acetate was prepared by reacting 35.8 grams of tricine and 31.6 grams of calcium acetate in 250 ml of water in a 500 ml three-neck flask equipped with a magnetic stirrer and reflux condenser. The solution was refluxed for three hours at which time the solution appeared clear. Water was evaporated to recover a waxy solid product of tricinatocalcium acetate.

EXAMPLE II(j)

Sarcosinatomagnesium acetate was prepared by reacting 8.9 grams of sarcosine and 21.5 grams of magnesium acetate tetrahydrate in 250 ml of water in a 500 ml three-neck flask equipped with a magnetic stirrer and reflux condenser. The solution was refluxed three hours at which time the solution appeared clear. The water was evaporated, and a white crunchy powder was recovered as sarcosinatomagnesium acetate.

EXAMPLE II(k)

Glycinatomagnesium acetate was prepared by reacting 7.5 grams of glycine and 21.5 grams of magnesium acetate tetrahydrate in 250 ml of water in a 500 ml three-neck flask equipped with a magnetic stirrer and reflux condenser. The solution was refluxed for three hours at which time the solution appeared clear. The water was evaporated to recover the product glycinatomagnesium acetate.

EXAMPLE II(l)

Zinc bis(bicinate) was prepared by reacting 21.9 grams of zinc acetate dihydrate and 32.6 grams of bicine in 250 ml of water in a 500 ml flask equipped with a magnetic stirrer and reflux condenser. The solution was refluxed for twenty-four hours and the water was then evaporated to recover the product zinc bis(bicinate).

EXAMPLE II(m)

Zinc bis(tricinate) was prepared by reacting 21.9 grams of zinc acetate dihydrate with 35.8 grams of tricine in 250 ml of water in a 500 ml flask equipped with a magnetic stirrer and reflux condenser. The solution was refluxed for twenty-four hours, and the water was then evaporated to recover a product of zinc bis(tricinate).

Similarly, glycinatotin (II) acetate, glycinatomanganese acetate, glycinatocadmium acetate and glycinatolead acetate are prepared following the steps as outlined in the above Examples by substituting an equivalent amount of tin acetate, manganese acetate, cadmium acetate and lead acetate, respectively, for the zinc acetate.

EXAMPLE III

The third reaction type is typified by the following equation:

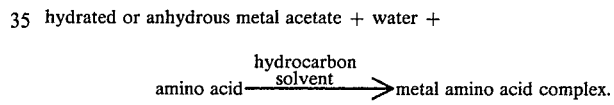

EXAMPLE III(a)

Glycinatozinc acetate.half-acetic acid, was prepared by adding 219.49 grams of zinc acetate dihydrate to 500 ml toluene in a two-liter reaction kettle equipped with a mechanical stirrer, reflux condenser, and a Dean-Stark Trap. Four ml of water were added to the stirring mixture. 75.07 grams of glycine and 500 ml of toluene were added to the mixture. The mixture was heated to reflux by an oil bath controlled to stay below 140° C. Water was collected immediately in a Dean-Stark Trap. Following an hour of reaction time, a solid mass formed at the bottom of the kettle. Stirring of the mixture became impossible after four hours of reaction time. The kettle was immediately immersed in an ice bath to facilitate removal of the product from the glass wall. A white chunky solid was filtered from the mixture, and upon drying, the solid was ground and rinsed with 200 ml of toluene through a vacuum filter. The product was dried in a forced air oven at about 70° C.

EXAMPLE III(b)

The above process was utilized to prepare glycinatozinc acetate.half-acetic acid by the substitution of mineral oil for toluene.

EXAMPLE III(c)

Glycinatostrontium acetate was prepared by reacting 51.42 grams of strontium acetate, 18.77 grams of glycine and 9.01 grams of water in 500 ml of xylene in a 1-liter round-bottom one-neck flask, equipped with a magnetic stirrer, reflux condenser and Dean-Stark Trap. The solution was heated at reflux temperature for six hours, and the solid product was isolated by filtration.

EXAMPLE IV

A fourth reaction type follows the equation:

hydrated metal acetate + amino acid + water +

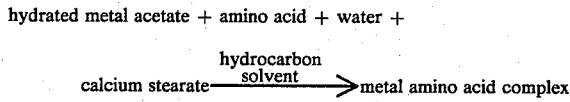
calcium stearate $\xrightarrow{\text{hydrocarbon solvent}}$ metal amino acid complex Glycinatozinc acetate.half-acetic acid, coated with calcium stearate was prepared by adding 15.18 grams of calcium stearate and 600 ml of toluene in a 2 liter, three-neck round-bottom flask equipped with a mechanical stirrer, reflux condenser and Dean-Stark Trap. 21.95 grams of zinc acetate dihydrate and 7.51 grams of glycine and 0.4 ml of water were added to the calcium stearate toluene solution. After heating the mixture at reflux temperature for three hours, the reaction mixture was cooled. The solvent was removed by rotary evaporation, and a powdery solid product was recovered from the reactor. The product was not hygroscopic.

EXAMPLE V

A fifth reaction type follows the equation:

organotin oxide + carboxylic acid +

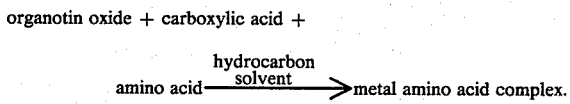
amino acid $\xrightarrow{\text{hydrocarbon solvent}}$ metal amino acid complex.

EXAMPLE V(a)

Dibutyltin glycinate stearate was prepared by adding 14.22 grams of stearic acid in 300 ml of toluene to a 500 ml one-neck round-bottom flask. The solution of stearic acid and toluene was warmed. Subsequently, 3.75 grams of glycine and 12.45 grams of dibutyltin oxide were added to the stearic acid toluene solution. The apparatus was equipped with magnetic stirrer, reflux condenser and Dean-Stark Trap. After prolonged refluxing, 0.9 ml of water was collected in the Dean-Stark Trap. The reaction was then stopped and the solvent was stripped to recover a waxy semi-solid product of dibutyltin glycinate stearate.

EXAMPLE V(b)

Dibutyltin methioninate stearate was prepared by dissolving 14.22 grams of stearic acid and 300 ml of toluene in a 500 ml one-neck, round-bottom flask equipped with a magnetic stirrer, reflux condenser and Dean-Stark Trap. The stearic acid toluene solution was warmed and, subsequently, 7.46 grams of methionine and 12.45 grams of dibutyltin oxide were added. After prolonged reflux, a quantitative amount of water was collected in the Dean-Stark Trap. The reaction was stopped, and the solvent stripped to recover the product of dibutyltin methioninate stearate.

EXAMPLE VI

A sixth reaction type follows the equation:

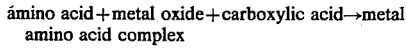
amino acid + metal oxide + carboxylic acid → metal amino acid complex

EXAMPLE VI(a)

Glycinatozinc stearate was prepared by reacting 8.14 grams of zinc oxide, 7.51 grams glycine, and 42.68 grams of stearic acid in 500 ml of toluene in a one-liter one-neck round-bottom flask equipped with a magnetic stirrer, reflux condenser and Dean-Stark Trap. The mixture was refluxed for 12 hours and then filtered hot. The filter cake was the product, glycinatozinc stearate. The filtrate, after removal of toluene, yielded 96% of the excess stearic acid.

EXAMPLE VI(b)

Glycinatobarium acetate was prepared by reacting 30.67 grams of barium oxide, 15.01 grams of glycine and 12.01 grams of acetic acid in 500 ml of xylene in a one liter, one-neck round-bottom flask equipped with a magnetic stirrer, reflux condenser and Dean-Stark Trap. The mixture was refluxed for six hours, and the solid product was isolated by filtration.

EXAMPLE VI(c)

Glycinatozinc octoate was prepared by reacting 16.3 grams of zinc oxide, 28.8 grams of octanoic acid and 15.0 grams of glycine in 500 ml of toluene in a one liter, one-neck round-bottom flask equipped with a magnetic stirrer, reflux condenser and Dean-Stark Trap. The mixture was refluxed for twenty-two hours, during which time water was collected in the Dean-Stark Trap. The toluene was stripped from the solution and the glycinatozinc octoate was recovered as a white paste.

EXAMPLE VI(d)

Glycinatozinc acetate was prepared by reacting 8.1 grams of zinc oxide, 6.0 grams of acetic acid and 7.5 grams of glycine in 500 ml of water in a one liter, one-neck flask, equipped with a magnetic stirrer and reflux condenser. The solution was refluxed for three hours. The water was evaporated and the solid product of glycinatozinc acetate was recovered.

EXAMPLE VI(e)

Glycinatozinc acetate.half-acetic acid was prepared by reacting 8.1 grams of zinc oxide, 9.0 grams of acetic acid and 7.5 grams of glycine in 500 ml of water. The apparatus was a one-liter, one-neck flask, equipped with a magnetic stirrer and reflux condenser. The solution was refluxed for three hours, and then the water was evaporated to recover the solid product of glycinatozinc acetate.half-acetic acid.

EXAMPLE VI(f)

Glycinatozinc acetate.20% barium stearate was prepared by ball-milling the glycinatozinc acetate as prepared in Example VI(d) with 20% by weight barium stearate overnight.

EXAMPLE VI(g)

Tryptophanatozinc acetate was prepared by reacting 20.4 grams of tryptophan, also known in the art as α-aminoindole-3-propionic acid as named in Merck Index, 9th Ed., Merck & Company, 1976, #9458 6.0 grams of acetic acid and 8.1 grams zinc oxide in 500 ml of water in a one-liter, one-neck round-bottom flask equipped with a condenser and magnetic stirrer. The solution was refluxed for three hours, and the solid product was isolated by evaporating the water.

EXAMPLE VI(h)

Glycinatozinc benzoate was prepared by reacting 12.2 grams of benzoic acid, 7.5 grams of glycine and 8.1 grams of zinc oxide in 1000 ml of water in a two-liter flask equipped with a magnetic stirrer and reflux condenser. The mixture was refluxed for two hours. The product was isolated by evaporation of the water.

EXAMPLE VI(i)

Zinc oxide glycinatozinc acetate was prepared by reacting 81.4 grams of zinc oxide, 30.0 grams of acetic acid and 37.5 grams of glycine in 500 ml of water in a one-liter flask equipped with a magnetic stirrer and reflux condensor. The mixture was refluxed for four hours. The product was recovered by the evaporation of the solvent.

EXAMPLE VI(j)

Zinc oxide glycinatozinc acetate.20% calcium stearate was prepared by ball-milling the zinc oxide glycinatozinc acetate as prepared in Example VI(i) with 20% by weight of calcium stearate overnight.

EXAMPLE VII

The seventh reaction type is typified by the following equation:

$$\text{metal oxide} + 2 \text{ amino acid} \rightarrow \text{metal amino acid complex.}$$

EXAMPLE VII(a)

Zinc bis(methyl-glutamate) was prepared by reacting 12.2 grams of zinc oxide and 48.3 grams of monomethyl-glutamate also known in the art as glutamic acid 5-methyl ester as named in C.A.S. Reg. No. 1499-55-4, pg. 458 Aldrich Catalog Handbook 1979-80 in 500 ml of toluene in a one-liter, one-neck round-bottom flask equipped with a magnetic stirrer, reflux condenser and Dean-Stark Trap. The mixture was refluxed to obtain a theoretical amount of water in the Dean-Stark Trap. A white powdery product was recovered by filtration.

EXAMPLE VII(b)

Zinc bis(bicinate) was prepared by reacting 8.1 grams of zinc oxide and 32.6 grams of bicine in 500 ml of water in a one-liter, one-neck flask equipped with a magnetic stirrer, and reflux condenser. The solution was refluxed for twenty-four hours and the solid product of zinc bis(bicinate) was recovered by filtration.

EXAMPLE VII(c)

Zinc bis(tricinate) was prepared by reacting 8.1 grams of zinc oxide and 35.8 grams tricine in 500 ml of water in a one-liter, one-neck round-bottom flask equipped with a magnetic stirrer and reflux condenser. The solution was refluxed for twenty-four hours, and the product was isolated by filtration.

EXAMPLE VII(d)

Barium bis(tricinate) was prepared by reacting 15.3 grams of barium oxide and 35.8 grams tricine in 500 ml of water in a one-liter, round-bottom flask equipped with a magnetic stirrer and reflux condenser. The solution was refluxed for twenty-four hours after which time the product, barium bis(tricinate), was recovered by evaporation of the solvent.

EXAMPLE VII(e)

Calcium bis(bicinate) was prepared by reacting 5.6 grams of calcium oxide with 32.6 grams of bicine in 500 ml of water in a one-liter, round-bottom flask equipped with a magnetic stirrer and a reflux condenser. The solution was refluxed for twenty-four hours, and the product was isolated by evaporation of the solvent.

EXAMPLE VIII

The eighth reaction type is typified by the following equation:

$$\text{zinc aminocarboxylate} + \text{carboxylic acid} \rightarrow \text{metal amino acid complex}$$

EXAMPLE VIII(a)

Glutamatozinc acetate was prepared by reacting 123.3 grams of zinc mono-glutamate dihydrate and 45.0 grams of acetic acid in a one-liter, one-neck flask with 500 ml of water. The apparatus was equipped with a magnetic stirrer and reflux condenser. The mixture was reacted at reflux temperature for twenty-four hours. The cloudy solution was filtered and the filtrate was stripped to recover the solid product, glutamatozinc acetate.

EXAMPLE VIII(b)

The process described in Example VIII(a) may be repeated, using various carboxylic acids, various solvent systems, and various zinc amino carboxylates.

EXAMPLE IX

The ninth reaction type is typified by the equation:

$$\text{zinc aminocarboxylate} + \text{amino acid} + \text{carboxylic acid} \rightarrow \text{metal amino acid complex}$$

EXAMPLE IX(a)

246.5 grams of zinc mono-glutamate dihydrate, 49.0 grams of glutamic acid also known as 2-aminopentanedioic acid as named in Merck Index, 9th Ed., Merck & Company, 1976, #4302 and 30.0 grams of acetic acid were added to 500 ml of water in a two-liter, three-neck flask. The apparatus was equipped with a magnetic stirrer and reflux condenser. The mixture was reacted at refluxing temperature for 48 hours. Water was removed by rotary evaporation, and a solid product consisting of zinc monoglutamate dihydrate, glutamatozinc acetate, and zinc di-glutamate was recovered.

EXAMPLE IX(b)

The amounts of zinc amino acid carboxylate, the amino acid and carboxylic acid may be varied in order to produce a zinc amino acid complex. The types of zinc amino carboxylates, amino acids, carboxylic acids and solvent systems may vary in order to produce the various zinc amino acid complexes.

TEST RESULTS

The following ten tables were prepared by utilizing the metal amino acid complexes of this invention in various amounts in combination with standard co-stabilizers in polyvinyl halide formulations. The parameters used for comparison are the time to first discoloration or when the resin system changes color, the time to dark or unacceptable color and the time to degradation or black color.

Samples for the testing were prepared by milling. Unplasticized polyvinyl chloride formulations were weighed out and hand-mixed thoroughly. The mixture was introduced on a two-roll mill (6"×12") at 350° F. The mixture was banded and mill mixed for four minutes, and further milled for one minute. Plasticized polyvinyl halide formulations were milled similarly, except that the roll temperature was maintained at 320° F.

Both plasticized and unplasticized polyvinyl halide formulations were tested by taking strips approximately ½"×10" of the formulation and subjecting them to an automatic time geared oven (Metrastat) or by manually retrieving square inch samples at definite time intervals from the oven. The samples may then be mounted on display cards for comparison. Unplasticized polyvinyl chloride formulations were tested for thirty or sixty minutes at 205° C. The plasticized polyvinyl halide formulations were tested for 120 minutes at 185° or 190° C.

Abbreviations used in the following tables are as follows:
DOP—dioctyl phthalate
ESO—epoxidized soybean oil
DPDP—diphenyl decyl phosphite
DHA—dehydroacetic acid
BHT—butylated hydroxy toluene
PE—pentaerythritol
GEON 103 EP F76—B. F. Goodrich polyvinyl chloride suspension resin
Diamond 450—Diamond Shamrock polyvinyl chloride suspension resin Table 1 shows the effect of the novel metal amino acid complex for a plasticized polyvinyl chloride formulation. The various formulations were subjected to heating at 185° C. for 120 minutes. Samples were taken every fifteen minutes. Specifically, Column 4 shows the effect of the novel metal amino acid complex of this invention, glycinatozinc stearate on the time to dark unacceptable color and time to degradation, as opposed to conventional zinc stabilizers as reported in Columns 2 and 3. Column 6 shows the effect of the present invention in combination with calcium stearate in prolonging the time to first discoloration, the time to dark unacceptable color and the time to degradation.

TABLE 1

|  | 1 | 2 | 3 | 4 | 5 | 6 |
|---|---|---|---|---|---|---|
| Geon 103 EP F76 | 100 | 100 | 100 | 100 | 100 | 100 |
| DOP | 40 | 40 | 40 | 40 | 40 | 40 |
| ESO | 5 | 5 | 5 | 5 | 5 | 5 |
| DPDP | 0.5 | 0.5 | 0.5 | 0.5 | 0.5 | 0.5 |
| Zinc stearate | — | 0.5 | — | — | — | — |
| Zinc glycinate/zinc stearate blend | — | — | 1.0 | — | 1.0 | — |
| Glycinatozinc stearate | — | — | — | 1.0 | — | 1.0 |
| Calcium stearate | — | — | — | — | 1.0 | 1.0 |
| Time to first discoloration | off the mill | 30 | 30 | 30 | 30 | 60 |
| Time to dark unacceptable color | 15 | 30 | 30 | 75 | 45 | 105 |
| Time to degradation, black color | >120 | 30 | 30 | 90 | 60 | 120 |

Table 2 details the times to coloration for a plasticized polyvinyl chloride formulation which was subjected to heating at 185° C. for 120 minutes. Samples were taken every 15 minutes. Column 5 shows the stabilizing effects that the novel metal amino acid complex of this invention has on a polyvinyl chloride formulation. Column 4 shows the effect of the glycinatozinc acetate.halfacetic acid when used as the sole stabilizer while Column 5 shows the effects when used with conventional co-stabilizers. Column 6 shows the results when conventional zinc stabilizers are used in conjunction with conventional co-stabilizers. Column 7 shows the results of the present invention used in conjunction with conventional co-stabilizers and pigments and fillers.

TABLE 2

|  | 1 | 2 | 3 | 4 | 5 | 6 | 7 |
|---|---|---|---|---|---|---|---|
| Geon 103 EP F76 | 100 | 100 | 100 | 100 | 100 | 100 | 100 |
| DOP | 40 | 40 | 40 | 40 | 40 | 40 | 40 |
| ESO | — | 1 | 1 | — | 1 | 1 | 1 |
| DPDP | — | 5 | 5 | — | 5 | 5 | 5 |
| DHA | — | 0.3 | 0.3 | — | 0.3 | 0.3 | 0.3 |
| BHT | — | 0.1 | 0.1 | — | 0.1 | 0.1 | 0.1 |
| PE | — | 0.1 | 0.1 | — | 0.1 | 0.1 | 0.1 |
| $TiO_2$ | — | — | 5 | — | — | — | 5 |
| $CaCO_3$ | — | — | 10 | — | — | — | 10 |
| Glycinatozinc acetate.half-acetic acid | — | — | — | 0.6 | 0.6 | — | 0.6 |
| Zinc glycinate/zinc acetate blend | — | — | — | — | — | 0.6 | — |
| Time to first discoloration | off the mill | 15 | 15 | 30 | 45 | 30 | 60 |
| Time to dark unacceptable color | 15 | 15 | 15 | 30 | 60 | 45 | 75 |
| Time to degradation, black color | 30 | 75 | 75 | 30 | 75 | 45 | 90 |

Table 3 lists the results of subjecting a polyvinyl chloride formulation to heating at 205° C. for 30 minutes. Samples were taken every five minutes. Column 1 shows the tendency of the polyvinyl chloride formulation to discolor immediately and produce black color after five minutes. Column 2 gives the figures for conventional zinc stabilizers whereas Column 3 shows an increase in the time to discoloration and degradation with the use of the novel metal amino acid complex of the present invention.

TABLE 3

|  | 1 | 2 | 3 | 4 |
|---|---|---|---|---|
| Diamond 450 | 100 | 100 | 100 | 100 |
| Stearic acid | 0.5 | 0.5 | 0.5 | 0.5 |
| Calcium stearate | 0.5 | 0.5 | 0.5 | 0.5 |
| $TiO_2$ | 5 | 5 | 5 | 5 |
| Zinc glycinate/zinc acetate blend | — | 0.6 | — | — |
| Glycinato zinc acetate. | — | — | 0.6 | — |

TABLE 3-continued

|  | 1 | 2 | 3 | 4 |
|---|---|---|---|---|
| half-acetic acid |  |  |  |  |
| Dehydroacetic acid | — | — | — | 0.6 |
| Time to first discoloration | off the mill | 5 | 10 | off the mill |
| Time to dark unacceptable color | 5 | 5 | 10 | 5 |
| Time to degradation, black color | 5 | 5 | 10 | 5 |

Table 4 gives the results of subjecting an unplasticized polyvinyl chloride formulation to heating at 205° C. for thirty minutes in the Metrastat oven. Column 2 shows the effect that dehydroacetic acid has on improving the stabilizing capabilities of the novel metal amino acid complex of the present invention. Columns 3 through 8 show the enhancing effects that butylated hydroxy toluene and pentaerythritol have on the stabilized resin system.

TABLE 4

|  | 1 | 2 | 3 | 4 | 5 | 6 | 7 | 8 |
|---|---|---|---|---|---|---|---|---|
| Diamond 450 | 100 | 100 | 100 | 100 | 100 | 100 | 100 | 100 |
| K120N (processing aid) | 0.6 | 0.6 | 0.6 | 0.6 | 0.6 | 0.6 | 0.6 | 0.6 |
| CaCO$_3$ | 5 | 5 | 5 | 5 | 5 | 5 | 5 | 5 |
| TiO$_2$ | 2 | 2 | 2 | 2 | 2 | 2 | 2 | 2 |
| Calcium stearate | 1 | 1 | 1 | 1 | 1 | 1 | 1 | 1 |
| Magnesium oxide | 1 | 1 | 1 | 1 | 1 | 1 | 1 | 1 |
| Glycinatozinc acetate. half-acetic acid | 1.5 | 1.5 | 1.5 | 1.5 | 1.5 | 1.5 | 1.5 | 1.5 |
| Dehydroacetic acid | — | 0.3 | 0.6 | 0.3 | 0.3 | 0.3 | 0.6 | — |
| BHT | — | — | — | 0.1 | — | 0.1 | 0.1 | 0.1 |
| PE | — | — | — | — | 0.1 | 0.1 | 0.1 | 0.1 |
| Time to first discoloration | off/mill | o/m | o/m | 13 | 13 | 13 | 12 | o/m |
| Time to degradation, black color | 13 | 20 | 20 | 30 | 30 | 30 | 30 | 30 |

Table 5 shows the results of subjecting an unplasticized polyvinyl chloride formulation to heating at 205° C. for 60 minutes in the Metrastat oven. Column 1 shows a control formulation without any stabilizers. Column 2 shows the stabilizing effects of glycinatozinc acetate.half-acetic acid. Column 3 shows the effects of glycinato calcium acetate. Column 4 shows the stabilizing effects of glycinato magnesium acetate and Column 5 shows the effects of glycinato strontium acetate.

TABLE 5

|  | 1 | 2 | 3 | 4 | 5 |
|---|---|---|---|---|---|
| Diamond 450 | 100 | 100 | 100 | 100 | 100 |
| Calcium stearate | 1.5 | 1.5 | 1.5 | 1.5 | 1.5 |
| Wax 165 (lubricant) | 1.0 | 1.0 | 1.0 | 1.0 | 1.0 |
| K120N (Processing aid) | 2.0 | 2.0 | 2.0 | 2.0 | 2.0 |
| KM323B (impact modifier) | 8.0 | 8.0 | 8.0 | 8.0 | 8.0 |
| TiO$_2$ | 15.0 | 15.0 | 15.0 | 15.0 | 15.0 |
| DHA | — | 0.3 | 0.3 | 0.3 | 0.3 |
| BHT | — | 0.1 | 0.1 | 0.1 | 0.1 |
| PE | — | 0.1 | 0.1 | 0.1 | 0.1 |
| Glycinatozinc acetate.half-acetic acid | — | 1.5 | 1.5 | 1.5 | 1.5 |
| Glycinato calcium acetate | — | — | 0.6 | — | — |
| Glycinato magnesium acetate | — | — | — | 0.9 | — |
| Glycinato stronium acetate | — | — | — | — | 1.3 |
| Time to first discoloration | off/mill | 30 | 30 | 30 | 30 |
| Time to degradation, black color | >60 | 35 | 40 | 40 | 30 |

Table 6 shows the results of subjecting unplasticized polyvinyl chloride formulations to heating at 205° C. for sixty minutes in the Metrastat oven. Column 1 shows the results for an unstabilized polyvinyl chloride formulation. Column 2 shows the results for a polyvinyl chloride formulation stabilized with glycinatozinc acetate.half-acetic acid, while Column 3 shows polyvinyl chloride stabilized with glycinatozinc acetate.acetic acid. Column 4 shows the stabilizing capabilities of a physical mixture of stabilizer components and Column 5 shows the stabilizing capability of the glycinatozinc acetate.half-acetic acid.10% calcium stearate.

TABLE 6

|  | 1 | 2 | 3 | 4 | 5 |
|---|---|---|---|---|---|
| Diamond 450 | 100 | 100 | 100 | 100 | 100 |
| Calcium stearate | 1.5 | 1.5 | 1.5 | 1.5 | 1.5 |
| Wax 165 (lubricant) | 1.0 | 1.0 | 1.0 | 1.0 | 1.0 |
| K120N (processing aid) | 2.0 | 2.0 | 2.0 | 2.0 | 2.0 |
| KM323B (impact modifier) | 8.0 | 8.0 | 8.0 | 8.0 | 8.0 |
| TiO$_2$ | 15.0 | 15.0 | 15.0 | 15.0 | 15.0 |
| DHA | — | 0.37 | 0.37 | 0.37 | 0.37 |
| BHT | — | 0.13 | 0.13 | 0.13 | 0.13 |
| PE | — | 0.13 | 0.13 | 0.13 | 0.13 |
| Glycinatozinc acetate.half-acetic acid | — | 1.87 | — | — | — |
| Glycinatozinc acetate.acetic acid | — | — | 1.87 | — | — |
| Glycine/zinc acetate dihydrate blend | — | — | — | 1.87 | — |
| Glycinatozinc acetate.half-acetic acid.10% calcium stearate | — | — | — | — | 1.87 |
| Time to first discoloration | off/mill | 35 | 30 | 20 | 40 |
| Time to degradation, black color | >60 | 40 | 35 | 20 | 45 |

Table 7 shows the results of subjecting a polyvinyl chloride formulation to heating at 205° C. for thirty minutes. Samples were taken every 5 minutes. Columns 1, 2, and 3 shows the stabilizing capabilities of novel metal amino acid complexes of the present invention which may be compared with the results of Columns 4 and 5 which show the stabilizing ability of a prior art example and a conventional stabilizer.

TABLE 7

|  | 1 | 2 | 3 | 4 | 5 |
|---|---|---|---|---|---|
| Diamond 450 | 100 | 100 | 100 | 100 | 100 |
| Stearic acid | 0.5 | 0.5 | 0.5 | 0.5 | 0.5 |
| Calcium stearate | 0.5 | 0.5 | 0.5 | 0.5 | 0.5 |
| TiO$_2$ | 5 | 5 | 5 | 5 | 5 |
| Zinc bis (α-amino laurate) | 1.48 | — | — | — | — |
| Zinc bis(glutamate) | — | 1.07 | — | — | — |
| Zinc bis(mono-methyl-glutamate) | — | — | 1.16 | — | — |
| Zinc bis(stearyl-lysinate)* | — | — | — | 2.67 | — |
| Dibutyltin maleate | — | — | — | — | 1.0 |
| Time to first discoloration | off/mill | 10 | 5 | off/mill | 10 |
| Time to dark, unacceptable color | 5 | 10 | 5 | 5 | 10 |
| Time to degradation, | 10 | 10 | 10 | 10 | 10 |

TABLE 7-continued

| | 1 | 2 | 3 | 4 | 5 |
|---|---|---|---|---|---|
| black color | | | | | |

*Synthesized according to Japan Kokai 77-31,021.

Table 8 shows the results of subjecting an unplasticized polyvinyl chloride formulation to heating at 205° C. for thirty minutes. Samples were taken every five minutes. Column 1 shows the unstabilized condition of the vinyl halide resin. Columns 2, 3, 4 and 5 detail the results for the use of zinc glycinate, zinc methioninate, zinc mono-glutamate dihydrate and zinc aspartate trihydrate, respectively, as stabilizers in the vinyl chloride resin. Columns 6 and 7 show the enhancing effect of dehydroacetic acid, butylated hydroxy toluene, and pentaerythritol on a vinyl halide resin stabilized by a metal amino acid complex of the present invention.

TABLE 8

| | 1 | 2 | 3 | 4 | 5 | 6 | 7 |
|---|---|---|---|---|---|---|---|
| Diamond 450 | 100 | 100 | 100 | 100 | 100 | 100 | 100 |
| Stearic acid | 0.5 | 0.5 | 0.5 | 0.5 | 0.5 | 0.5 | 0.5 |
| Calcium stearate | 0.5 | 0.5 | 0.5 | 0.5 | 0.5 | 0.5 | 0.5 |
| TiO$_2$ | 5 | 5 | 5 | 5 | 5 | 5 | 5 |
| Glycidyl-p-methoxy phenyl ether | 0.54 | 1.0 | 1.0 | 1.0 | 1.0 | — | — |
| Stearyl neopentylene phosphite | — | 1.0 | 1.0 | 1.0 | 1.0 | — | — |
| DPDP | — | — | — | — | — | 1 | 1 |
| ESO | — | — | — | — | — | 5 | 5 |
| CaCO$_3$ | — | — | — | — | — | 10 | — |
| Zinc glycinate | — | 0.64 | — | — | — | — | — |
| Zinc methioninate | — | — | 1.08 | — | — | — | — |
| Zinc mono-glutamate dihydrate | — | — | — | 0.75 | — | 2.0 | 2.0 |
| Zinc aspartate trihydrate | — | — | — | — | 0.75 | — | — |
| DHA | — | — | — | — | — | 0.3 | 0.3 |
| BHT | — | — | — | — | — | 0.1 | 0.1 |
| PE | — | — | — | — | — | 0.1 | 0.1 |
| Time to first discoloration | off/mill | 5 | 10 | 10 | 5 | 15 | 15 |
| Time to dark, unacceptable color | 5 | 10 | 10 | 10 | 5 | 20 | 20 |
| Time to degradation, black color | 5 | 15 | 15 | 15 | 15 | 30 | 30 |

Table 9 shows the effect of subjecting a plasticized polyvinyl chloride formulation to heating at 185° C. for 120 minutes. Samples were taken every 15 minutes. Column 1 shows the tendency of the vinyl halide resin to discolor without any stabilizers. Column 2 shows the stabilizing effect of zinc bis(glutamate). Column 3 shows the stabilizing effects of zinc bis(glutamate) in combination with calcium bis(glutamate) monohydrate. Column 4 shows the effect of increasing calcium bis(glutamate) monohydrate in the formulation of Column 3. Column 5 shows the effect of a further increase of the calcium bis(glutamate) monohydrate in the system. Column 6 shows the effect of zinc bis(glutamate) used in conjunction with magnesium bis(glutamate).

TABLE 9

| | 1 | 2 | 3 | 4 | 5 | 6 |
|---|---|---|---|---|---|---|
| Geon 103 EP F76 | 100 | 100 | 100 | 100 | 100 | 100 |
| DOP | 40 | 40 | 40 | 40 | 40 | 40 |
| DPDP | 1 | 1 | 1 | 1 | 1 | 1 |
| ESO | 5 | 5 | 5 | 5 | 5 | 5 |
| DHA | — | 0.3 | 0.3 | 0.3 | 0.3 | 0.3 |
| BHT | — | 0.1 | 0.1 | 0.1 | 0.1 | 0.1 |
| PE | — | 0.1 | 0.1 | 0.1 | 0.1 | 0.1 |
| Zinc bis(glutamate) | — | 0.7 | 0.7 | 0.7 | 0.7 | 0.7 |
| Calcium bis(glutamate) monohydrate | — | — | 0.1 | 0.3 | 0.5 | — |
| Magnesium bis(glutamate) | — | — | — | — | — | 0.1 |
| Time to first discoloration | off/mill | 15 | 15 | 15 | 15 | 15 |
| Time to dark, unacceptable color | 15 | 90 | 75 | 90 | 90 | 90 |
| Time to degradation, black color | >120 | 105 | 90 | 90 | 105 | 105 |

Table 10 shows the effects of subjecting a plasticized formulation of polyvinyl chloride to heating at 190° C. for 120 minutes in the Metrastat oven. Column 1 shows the stabilizing capabilities of a barium-cadmium commercial stabilizer. Column 2 shows the stabilizing effects of zinc bis(bicinate). Column 3 shows the stabilizing effects of tricinatozinc acetate. Columns 4 and 5 show the stabilizing effects of the reaction product of Example IX(a). Column 6 shows the stabilizing capability of glutamatozinc acetate. Column 8 shows the stabilizing capabilities of glutamatozinc acetate used in conjunction with both zinc mono-glutamate dihydrate and zinc bis(glutamate).

TABLE 10

| | 1 | 2 | 3 | 4 | 5 | 6 | 7 | 8 | 9 | 10 |
|---|---|---|---|---|---|---|---|---|---|---|
| Geon 103 EP F76 | 100 | 100 | 100 | 100 | 100 | 100 | 100 | 100 | 100 | 100 |

TABLE 10-continued

|  | 1 | 2 | 3 | 4 | 5 | 6 | 7 | 8 | 9 | 10 |
|---|---|---|---|---|---|---|---|---|---|---|
| DOP | 40 | 40 | 40 | 40 | 40 | 40 | 40 | 40 | 40 | 40 |
| DPDP | 1 | 1 | 1 | 1 | 1 | 1 | 1 | 1 | 1 | 1 |
| ESO | 5 | 5 | 5 | 5 | 5 | 5 | 5 | 5 | 5 | 5 |
| Therm-Chek* 1827 |  |  |  |  |  |  |  |  |  |  |
| Ba/Cd commercial stabilizer | 1 | — | — | — | — | — | — | — | 1 | — |
| DHA | — | 0.3 | 0.3 | — | 0.3 | 0.3 | 0.3 | 0.3 | — | 0.3 |
| BHT | — | 0.1 | 0.1 | — | 0.1 | 0.1 | 0.1 | 0.1 | — | 0.1 |
| PE | — | 0.1 | 0.1 | — | 0.1 | 0.1 | 0.1 | 0.1 | — | 0.1 |
| Zinc bis(bicinate) | — | 1.0 | — | — | — | — | 1.0 | — | — | — |
| Tricinatozinc acetate | — | — | 0.1 | — | — | — | — | — | — | — |
| Reaction product of Example IX(a) | — | — | — | 0.88 | 0.88 | — | — | — | — | — |
| TiO$_2$ | — | — | — | — | 5 | 5 | 5 | 5 | 5 | 5 |
| CaCO$_3$ | — | — | — | — | 10 | 10 | 10 | 10 | 10 | 10 |
| Glutamatozinc acetate | — | — | — | — | — | 0.8 | — | 0.27 | — | — |
| Zinc mono-glutamate dihydrate | — | — | — | — | — | — | — | 0.25 | — | — |
| Zinc bis(glutamate) | — | — | — | — | — | — | — | 0.36 | — | — |
| ZnO.glyZnO Ac.20% Ca Str$_2$ |  |  |  |  |  |  |  |  |  | 0.84 |
| Time to first discoloration | 90 | 90 | 90 | 95 | 110 | 110 | 90 | 105 | 90 | 60 |
| Time to degradation, black color | >120 | >120 | 110 | 95 | 110 | 110 | 120 | 105 | 120 | 60 |

*Therm-Chek is a commercial product of Ferro Corporation, Bedford Chemical Division

What is claimed is:

1. A compound having the general formula:

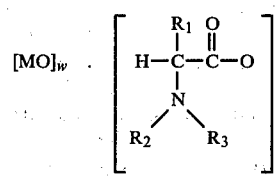

wherein w has a value of 0-2;

M is a member selected from the group of divalent metals consisting of zinc, magnesium, calcium, barium, strontium, manganese, cadmium, lead, tin II, tin IV(R$_5$)$_2$ where R$_5$ is a lower alkyl of C$_1$-C$_8$;

R$_1$ is a member selected from the group consisting of H—, C$_1$-C$_{12}$ alkyl,

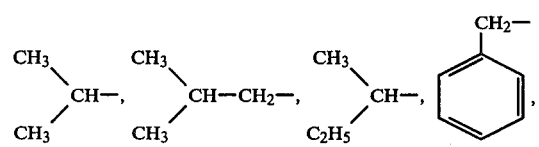

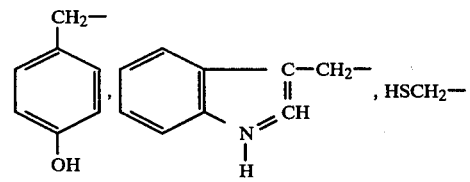

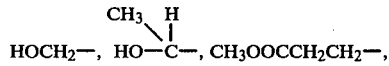

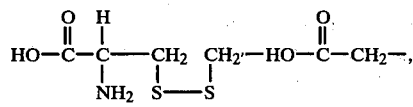

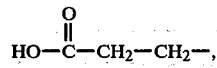

-continued

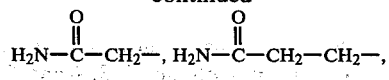

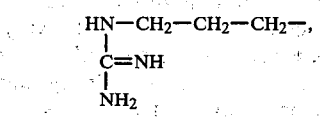

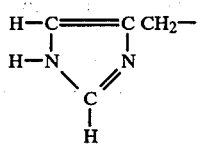

and CH$_3$SCH$_2$CH$_2$— with the proviso that R$_1$ cannot be CH$_3$SCH$_2$CH$_2$— when M is zinc;

R$_2$ is a member selected from the group consisting of H, CH$_2$CH$_2$OH, C(CH$_2$OH)$_3$, an alkyl of C$_1$-C$_{15}$ and an aryl ring;

R$_3$ is a member selected from the group consisting of H and CH$_2$CH$_2$OH;

R$_4$ is a member selected from the group consisting of alkyls of C$_1$-C$_{20}$, straight chain or branched, an aryl and substituted aryl; and Z is 0-1 molecules or partial molecules of a carboxylic acid corresponding to HOOCR$_4$.

2. A compound according to claim 1 wherein M is selected from the group consisting of zinc, magnesium, calcium, barium, manganese and strontium.

3. A compound according to claim 1 wherein M is selected from the group consisting of zinc, calcium and barium.

4. A compound according to claim 1 wherein M is zinc.

5. A compound according to claims 2, 3 or 4 wherein W is 0.

6. A compound according to claims 2, 3 or 4 wherein W is greater than 0 but not greater than 2.

7. A compound according to claim 6 which is zinc oxide glycinatozinc acetate.

8. A compound having the general formula

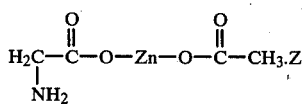

wherein Z is 0-1 moles or partial moles of acetic acid.

9. A compound according to claim 8 which is glycinatozinc acetate.acetic acid.

10. A compound according to claim 8 which is glycinatozinc acetate.half acetic acid.

11. A compound according to claim 1 which is glutamatozinc acetate.

12. A compound according to claim 1 which is tricinatozinc acetate.

13. A compound according to claim 1 which is bicinatozinc acetate.

* * * * *